United States Patent [19]

Kasai

[11] Patent Number: 5,652,443
[45] Date of Patent: Jul. 29, 1997

[54] SENSOR HAVING A MICRO-BRIDGE HEATER

[75] Inventor: Fumio Kasai, Miki, Japan

[73] Assignee: Ricoh Company, Inc., Tokyo, Japan

[21] Appl. No.: 513,594

[22] Filed: Aug. 10, 1995

[30] Foreign Application Priority Data

Aug. 10, 1994 [JP] Japan .................................. 6-210369
Nov. 4, 1994 [JP] Japan .................................. 6-295581

[51] Int. Cl.$^6$ .................................................. H01L 23/58
[52] U.S. Cl. ................ 257/252; 257/253; 257/414; 422/95; 422/97; 422/98; 338/34; 73/23.24
[58] Field of Search .............................. 257/252, 253, 257/414; 422/97, 98, 95; 338/34; 73/23.24

[56] References Cited

U.S. PATENT DOCUMENTS

| | | | |
|---|---|---|---|
| 4,343,768 | 8/1982 | Kimura | 422/97 |
| 4,791,465 | 12/1988 | Sakai et al. | 257/414 |
| 4,967,589 | 11/1990 | Yagawara et al. | 73/23.25 |
| 5,003,812 | 4/1991 | Yagawara et al. | 73/31.06 |

FOREIGN PATENT DOCUMENTS 57-94641 12/1982 Japan .

Primary Examiner—William Mintel
Attorney, Agent, or Firm—Oblon, Spivak, McClelland, Maier & Neustadt, P.C.

[57] ABSTRACT

A sensor including a micro-bridge heater which is located above a depression in the surface of a substrate. The heater includes a first insulating film on the substrate, a conductive film on the first insulating film, and a second insulating film on the conductive film. The first and second insulating films are made of the same material, preferably tantalum oxide ($Ta_2O_5$) and are the same thickness. A foundation film is not employed as an adhesive between the first insulating film and the conductive film due to the strong adherence between the first insulating film and the conductive film which is preferably made of platinum or a platinum alloy. Because the first and second insulating films are made of the same material and have the same thicknesses, the insulating films have similar rates of thermal expansion and the expansion or contraction of the insulating films offset each other, thus reducing the thermal stress imposed on the conductive film.

9 Claims, 3 Drawing Sheets

SENSOR HAVING A MICRO-BRIDGE HEATER

BACKGROUND OF THE INVENTION

1. Field of the Invention

The present invention relates to integrated device sensors. More specifically, the present invention relates to sensors having a bridge structure in which an electrical resistance changes in response to ambient conditions. The sensor may be used for flow sensing, humidity sensing, infrared ray sensing, or gas sensing.

2. Discussion of the Background

In recent years, flow measuring such as hygrometry and gas measurement has been performed by utilizing a phenomenon which makes the electric properties of a conductive film used as a sensing portion of a sensor change with changing humidity or density of the gas. For example, a change of humidity in the atmosphere may be expressed as a change of the heat conductivity rate of a conductive film. Therefore, an apparatus utilizing this phenomenon can detect the change of humidity or other changes by measuring a resistance change of the heater which is made of a film having known properties. This change in resistance corresponds to a temperature change of the heater. The heater is heated by applying an electric current intermittently or continuously to the conductive film.

In order to have a low thermal time constant and to stabilize the performance of the heater, the heating portion is separated from a supporting substrate such as a silicon substrate by suspending the heating portion of the substrate in a bridge-like manner. Due to the small size and bridge-like construction, the heater is commonly referred to as a micro-bridge heater.

The micro-bridge heater includes a substrate, a first insulating film formed on the substrate, a conductive film made of a selected material formed on the first insulating film, and a second insulating film formed on the conductive film. These three films form the heating portion of the heater. One or both ends of the heating structure are fixed on the substrate and a center portion of the heating structure is separated from the substrate due to a depression which is formed in the substrate.

An exemplary conventional method of fabricating a micro-bridge heater made of thin films is disclosed in Japanese Laid-Open Patent Application No. 57-94641 which is incorporated herein by reference. The structure of this conventional micro-bridge heater is explained referring to FIGS. 1–3. FIG. 1 illustrates a top view of the micro-bridge heater, FIG. 2 illustrates a cross-sectional view at line X–X' of FIG. 1, and FIG. 3 shows a cross-sectional view at line Y–Y' of FIG. 1.

The conventional device of FIGS. 1–3 is an integrated semiconductor device including a semiconductor substrate 1 made of a material such as silicon having a depression 10 formed therein, as shown in FIGS. 2 and 3. There is a first insulating film 2 formed on the semiconductor body 1, a foundation metal film 3 formed thereon, a conductive film 4 formed on the foundation metal film 3, and a second insulating film 5 formed on the conductive film 4. These four films form a heating portion bridging the depression 10. Parts of these films are removed selectively, for example by etching, which results in the structure illustrated in FIGS. 1–3. The conductive film 4 has electrical current applied thereto and generates heat.

The conductive film 4 is a platinum film which is 5,000 angstroms thick, and a silicon dioxide ($SiO_2$) film having a thickness of 1.4 microns is used as the first insulating film 2. The foundation metal film 3 is made of a metal such as molybdenum, titanium or chromium, has a thickness of 400 angstroms, and functions to increase adhesivity between the first insulating film 2 and the conductive film 4. The second insulating film 5 is made of silicon dioxide ($SiO_2$) and has a thickness of about 3,000 angstroms. Both ends of the heating portion 7 are fixed on the semiconductor body 1. These ends are formed as electrode pads 8. When the conventional micro-bridge heater described above is used as a humidity sensor, electric power, for example 10 mW, is applied to the electrode pads 8 of the heating portion 7 in the form of pulses. The pulses having a minimum duration of 50 milliseconds to 100 milliseconds are applied every fixed cycle such as 1 second to 1 minute in the case of a humidity sensor and then the voltage across the pads 8 is measured. The measured voltage is typically several millivolts and this voltage is amplified by a suitable amplifier (not illustrated).

A problem exists in that the pulses of the electrical power cause thermal stress due to the rise in temperature of the heating portion to about 400° C. and a subsequent falling towards an ambient temperature. Because this thermal stress occurs intermittently, cracks are generated at the heating portion 7 at an interface between the conductive film 4 and the first insulating film 2, and between the conductive film 4 and the second insulating film 5. This may cause separation of the films depending on the circumstances. When silicon nitride is used as the insulating films 2 or 5, crack production increases. This is because a silicon nitride film has a high internal stress and thermal expansion problems. Furthermore, warp caused by repeated expansion and contraction of the films also produces cracks due to thermal stress.

The thermal stress and cracks are not only caused by heat generated by the micro-bridge heater itself but also by changes in ambient temperature. A temperature increase at a location where the micro-bridge heater is located has detrimental effects similar to the thermal stress due to heat generation by the micro-bridge heater, and therefore cracks and thermal stress may occur even if electric power is not applied to the heater.

The thickness of the second insulating film 5 of the micro-bridge heater shown in FIG. 1 is as thin as 3,000 angstroms. The small thickness of the second insulating film 5 reduces a covering ability of the second insulating film over the conductive film 4. This makes the separation of the second insulating film from the conductive film easier when a pulse of current is applied across the conductive film 4. Also, the small thickness of the second insulating film 4 increases the amount of oxygen which can permeate through the second insulating film, thus increasing oxidation of the conductive film 4. Therefore the lifetime of the micro-bridge heater may be short due to thermal stress caused by repeated application electric pulses. Further, applying electric pulses repeatedly in normal use causes thermal oxidation of the conductive film 4 due to thermal stress.

SUMMARY OF THE INVENTION

Accordingly, one object of this invention is to provide a sensor including a micro-bridge heater that has a lower internal stress, and a high tolerance to thermal stress.

Another object of this invention is to provide a micro-bridge heater in which the second insulating film protects from oxidation.

These and other objects are accomplished by a sensor including a bridge heater. The sensor is constructed to have a heating portion bridging a depression in a substrate to which the heating portion is mounted. The heating portion includes a first insulating film mounted directly on the substrate, a conductive film mounted on the first insulating film, and a second insulating film on the conductive film. Preferably, the first and second insulating films are made of tantalum oxide ($Ta_2O_5$) of the same thickness. The conductive film is made of platinum or a platinum alloy.

Both the second insulating film and conductive film may be covered with a third insulating film made of the same material as the second insulating film.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 4:
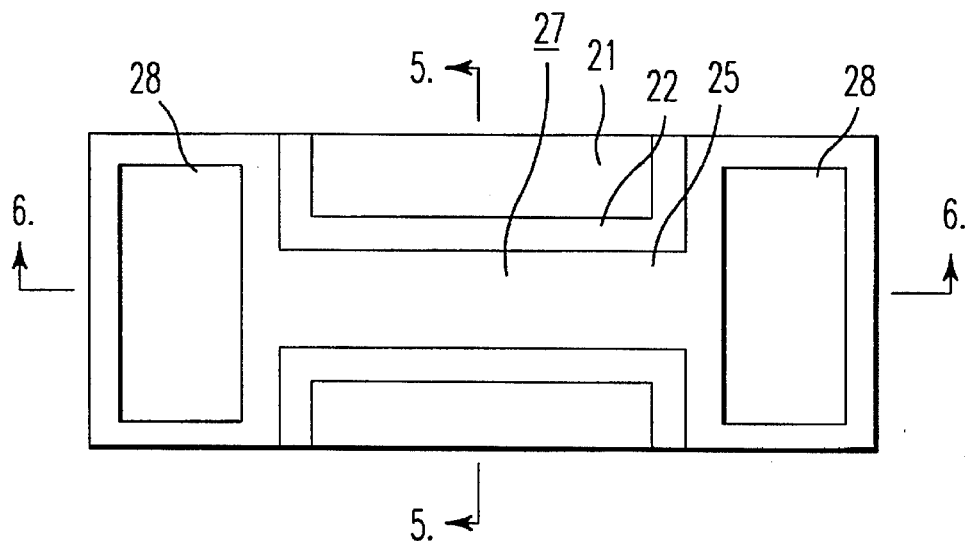
FIG. 4 is a top view of a sensor including a micro-bridge heater constructed according to the present invention.
Figure 5:
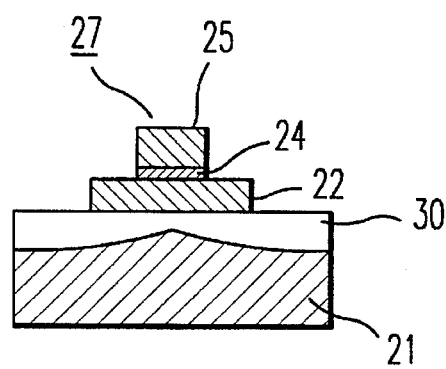
FIG. 5 is a cross-sectional view at line U–U' of the sensor shown in FIG. 4.
Figure 6:
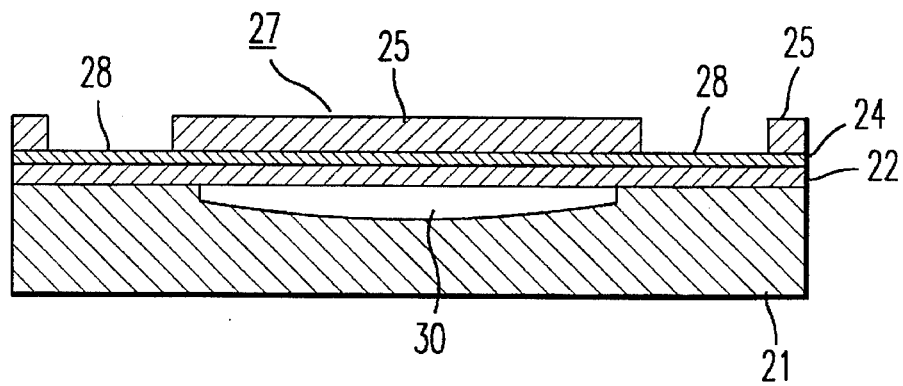
FIG. 6 is a cross-sectional view at line V–V' of the sensor shown in FIG. 4.

Referring now to the drawings, wherein like reference numerals designate identical or corresponding parts throughout the several views and more particularly to FIGS. 4–6 thereof, there is illustrated a sensor including a micro-bridge heater constructed according to the present invention. FIG. 4 shows a top view of the sensor, FIG. 5 shows a cross-sectional view at line U–U' of FIG. 4, and FIG. 6 shows a cross-sectional view at line V–V' of FIG. 4. In FIGS. 4–6, there is illustrated a semiconductor substrate 21 such as silicon having a first surface with a depression 30 formed therein, as illustrated in FIGS. 5 and 6. There is a first insulating film 22 formed on the semiconductor body 21, a conductive film 24 formed directly on the first insulating film 22, and a second insulating film 25 formed on the conductive film 24. The first insulating film 22, the conductive film 24, and the second insulating film 25 form a heating portion 27.

The conductive film 24 is preferably a platinum or platinum alloy film which is 5,000 angstroms thick. The first insulating film 22 and the second insulating film 25 are formed of tantalum oxide ($Ta_2O_5$) and have the same thickness of approximately 1.25 microns but may be in the range between 1.0 and 1.5 microns in thickness. The sensor is about 165 microns in width, 165 microns in length and the height depends on the thickness of the semiconductor body 21. The depth of the depression ranges from 150 microns to 250 microns. The first insulating film 22 must have sufficient mechanical strength to support the heating portion 27 over the depression 30. Further, the second insulating film 25 must cover the conductive film 24 and protect the conductive film 24 against oxidation.

Figure 1:
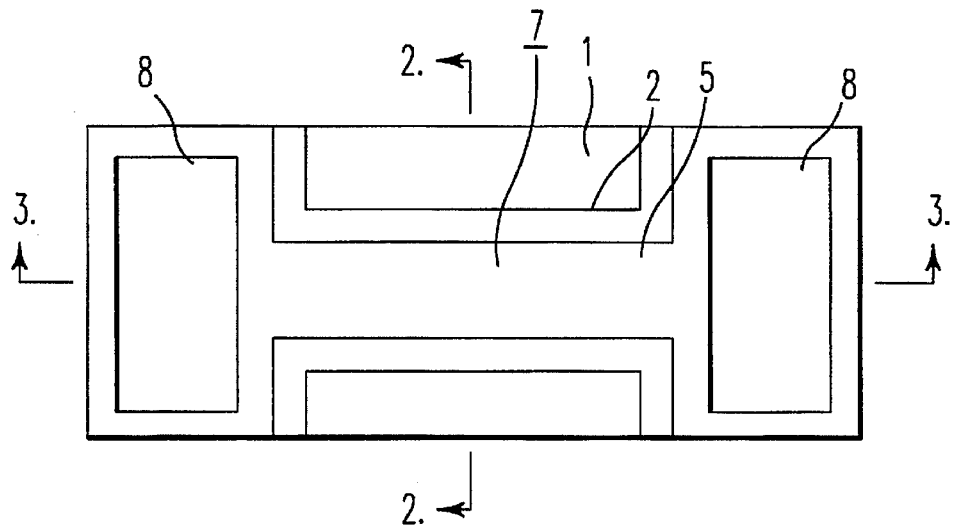
FIG. 1 is a top view of a conventional sensor including a micro-bridge heater.
Figure 2:
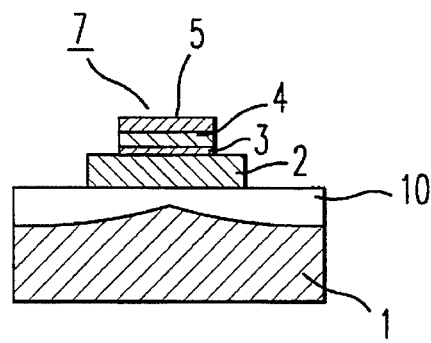
FIG. 2 is a cross-sectional view at line X–X' of the sensor shown in FIG. 1.
Figure 3:
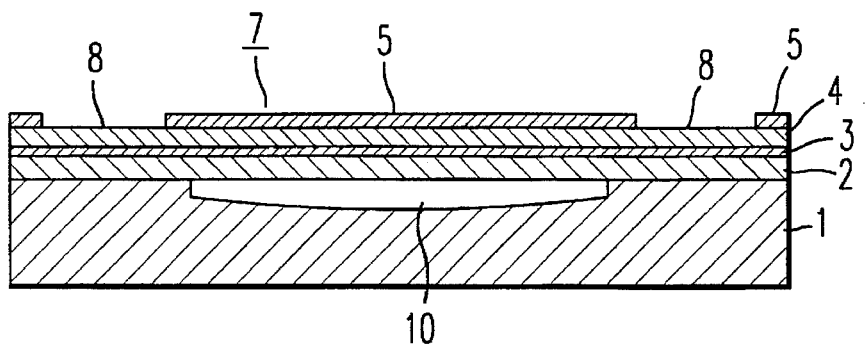
FIG. 3 is a cross-sectional view at line Y–Y' of the sensor shown in FIG. 1.

Tantalum oxide ($Ta_2O_5$) is used as the first and second insulating films because of its properties including a low amount of thermal expansion in response to an increase in temperature, low internal stress (e.g. changes in size due to thermal changes), and high resistivity to cracking. Furthermore, a tantalum oxide film is highly adhesive to both platinum and silicon and is therefore suitable as a connecting film between the silicon semiconductor body 21 and the platinum or platinum alloy conductive film 24. Therefore, even though the present invention does not use an adhesive or foundation metal film such as film 3 illustrated in FIGS. 2 and 3, there are no separation problems between the conductive film 24 and the insulating film 22.

Both ends of the heating portion 27 are fixed on the silicon body 21, although it is possible to have only one of the heating portion 27 fixed to the silicon body 21. Electrode pads 28 are connected to each end of the heating portion 27 in order to apply an electric current and to measure the voltage across the heating portion.

The method of fabricating the present invention is similar to the fabrication of the device disclosed in Japanese Laid-Open Patent Application No. 57-94641. The method of fabrication and features of the invention can also be created according to the teachings set forth in U.S. Pat. No. 4,343, 768, which is incorporated herein by reference. The present invention is constructed by starting with the silicon substrate 21. Sputtering is used to form the first insulating film 22 using tantalum oxide, a platinum (Pt) film and then the second insulating film 25 are formed by spattering thereon. Etching is performed in order to construct the layers as illustrated in FIGS. 4–6. Furthermore, etching of the silicon semiconductor body 21 is performed in order to form the depression 30 as illustrated in FIGS. 5 and 6. The portions above the electrode pads 28 are also etched in order to expose the conductive film 24 at the electrode pads 28. The depression 30 creates a space and allows gases or liquids to pass between the underside of the heating portion 27 and the semiconductor body 21. This allows the thermal time constant of the device to be reduced.

Figure 7:
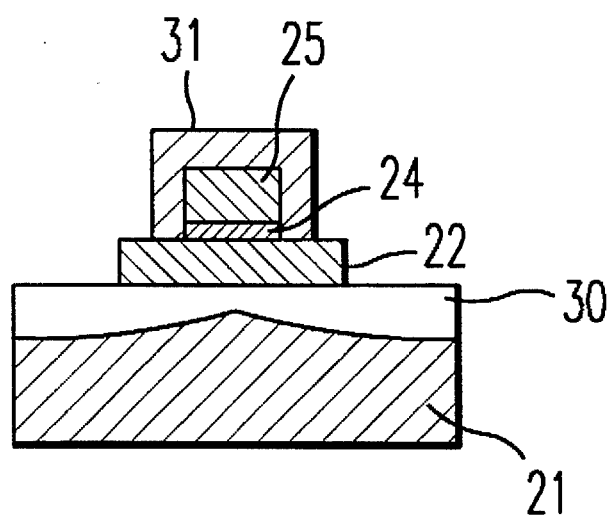
FIG. 7 is a cross-sectional view of a sensor having a third insulating film surrounding the second insulating film.

As a variation of and an addition to the embodiment disclosed in FIGS. 4–6, a third insulating film 31 can be used to cover both the second insulating film 25 and both sides of the conductive film 24, as illustrated in FIG. 7. The third insulating film 31 provides additional protection to the conductive film 24 against oxidation which is a characteristic deterioration. The third insulating film 31 is preferably formed of tantalum oxide ($Ta_2O_5$) by spattering and the construction of the embodiment illustrated in FIG. 7 is similar to the construction of the embodiment illustrated in FIGS. 4–6, except for the addition of the third insulating film 31. The embodiment of FIG. 7 may also be constructed based on the teachings of JP 57-94641.

In addition to using tantalum oxide ($Ta_2O_5$) as the first, second, and third insulating films in either of the embodiments, silicon dioxide ($SiO_2$) or silicon nitride ($Si_3N_4$) may also be used for these insulating films.

In the present invention, there is no foundation film serving as an adhesive between the first insulating film 22 and the conductive film 25 and the first insulating film 22 and the second insulating film 25 are formed of the same material. Therefore, resistance to heat, rates of expansion due to heat applied to the first and second insulating films which sandwich the conductive film 24 and other effects on the insulating films are the same. Accordingly, expansion or contraction of the insulating films 22 and 25 offset each other. This reduces the thermal stress imposed upon the conductor 24. Further, by having the first and second insulating films the same thickness, expansion or contraction of these films offset each other and reduce thermal stress. Additionally, the second insulating film 25 and the first insulating film 22 also prevent oxidation of the conductive film 24.

The use of oxide films of silicon or tantalum for both the first insulating film 22 and the second insulating film 25 makes it possible to reduce the internal stress of the conductive film 24. As can be seen in FIGS. 5–7, the first insulated film 22 has portions thereof directly exposed to the ambient environment and other portions contacting the conductive film 24 or the substrate 21. This causes different portions of the first insulating film 22 to be exposed to different temperatures. The portions at different temperatures may cause separation or cracks due to different expansions. The inventors have determined that tantalum oxide has much less of a problem with different amounts of thermal expansion as compared to a conventional insulating material such as silicon nitride. Furthermore, covering the sides of the conductive film 24 by the third insulating film 31, especially by the oxide film of silicon-metal compound or tantalum-metal compounds makes it possible to prevent the conductive film 24 from oxidizing. All of the above features allow the present invention to have a longer life as compared to conventional sensors employing a micro-bridge heater.

The construction of the present invention is applicable to any sensor using a micro-bridge heater including, but not limited to, a gas sensor, humidity sensor, or infrared ray sensor.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A sensor comprising:

a substrate which has a depression on a surface thereof;

a first insulating film made of tantalum oxide formed on said surface of said substrate;

a conductive film used as a sensing portion formed on said first insulating film, said conductive film having a terminal located at each of two ends of the conductive film; and a second insulating film made of tantalum oxide formed on said conductive film to cover said conductive film, wherein said first insulating film and said second insulating film have a same thickness.

2. A sensor according to claim 1, wherein:

said conductive film includes platinum.

3. A sensor according to claim 1, wherein:

said first insulating film has two ends, each of said two ends of the first insulating film being attached to said substrate.

4. A sensor according to claim 1, wherein said same thickness is 1.0 microns to 1.5 microns.

5. A sensor according to claim 1, further comprising:

a third insulating film covering sides of the conductive film.

6. A sensor according to claim 5, wherein:

said third insulating film also covers a top of the second insulating film and sides of the second insulating film, the top of the second insulating film being opposite to a bottom of the second insulating film which contacts the conductive film.

7. A sensor comprising:

a substrate which has a depression on a surface thereof;

a first insulating film made of tantalum oxide formed on said surface of said substrate;

a conductive film used as a sensing portion formed on said first insulating film, said conductive film having a terminal located at each of two ends of the conductive film; and a second insulating film made formed on said conductive film to cover the conductive film, the second insulating film being made of a same material as the first insulating film is made, a thickness of the second insulating film being equal to a thickness of the first insulating film.

8. A sensor according to claim 1, further comprising:

a third insulating film covering sides of the conductive film.

9. A sensor according to claim 7, wherein:

said third insulating film also covers a top of the second insulating film and sides of the second insulating film, the top of the second insulating film being opposite to a side of the second insulating film which contacts the conductive film.

* * * * *

UNITED STATES PATENT AND TRADEMARK OFFICE
CERTIFICATE OF CORRECTION

PATENT NO. : 5,652,443
DATED : July 29, 1997
INVENTOR(S) : Fumio KASAI

It is certified that error appears in the above-indentified patent and that said Letters Patent is hereby corrected as shown below:

On the title page, item [73], the assignee should read:
--Ricoh Company, Ltd.--

Signed and Sealed this

Twenty-fifth Day of November, 1997

Attest:

BRUCE LEHMAN

Attesting Officer

Commissioner of Patents and Trademarks